(12) United States Patent
Hauschildt

(10) Patent No.: US 7,599,806 B2
(45) Date of Patent: Oct. 6, 2009

(54) PORTABLE POWER METER FOR CALCULATING POWER APPLIED TO A PEDAL AND CRANK ARM BASED DRIVE MECHANISM AND A METHOD OF CALCULATING THE POWER

(75) Inventor: Gunter Michael Hauschildt, Ottawa (CA)

(73) Assignee: Gunter Hauschildt, Ottawa, Ontario ( * ) Notice: Subject to any disclaimer, the term of this patent is extended or adjusted under 35 U.S.C. 154(b) by 327 days.

(21) Appl. No.: 11/276,885

(22) Filed: Mar. 17, 2006

(65) Prior Publication Data

US 2007/0245835 A1   Oct. 25, 2007

(51) Int. Cl.
G01L 5/00 (2006.01)
(52) U.S. Cl. .................................. 702/44; 73/379.07
(58) Field of Classification Search .................. 702/33, 702/41, 42, 44, 85
See application file for complete search history.

(56) References Cited

U.S. PATENT DOCUMENTS

| | | | |
|---|---|---|---|
| 4,423,630 A | 1/1984 | Morrison | |
| 5,031,455 A | 7/1991 | Cline | |
| 6,199,021 B1 | 3/2001 | Cote | |
| 6,272,936 B1 | 8/2001 | Oreper | |
| 6,356,848 B1 | 3/2002 | Cote | |
| 6,684,713 B2 * | 2/2004 | Nissila | 73/775 |
| 2006/0248965 A1 * | 11/2006 | Wyatt et al. | 73/862.391 |

OTHER PUBLICATIONS

Caldwell, G. E. et al. "Pedal and Crank Kinetics in Uphill Cycling", (1993), Journal of Applied Biomechanics, vol. 14, pp. 245-259.*
Cavanagh PR, Sanderson DJ (1986). The biomechanics of cycling: Studies of the pedaling mechanics of elite pursuit riders. In: *Science of Cycling*, Human Kinetics Books, Champaign, ch5.
Smak, W, Neptune RR, Hull, ML (1999). The influence of pedaling rate on bilateral asymmetry in cycling. *Journal of Biomechanics, 32*, 899-906.
Caldwell GE, Li L, McCole SD, Hagberg JM (1998). Pedal and Crank Kinetics in Uphill Cycling. *Journal of Applied Biomechanics, 14* 245-259.
Stone C, Hull ML (1993). Rider/bicycle interaction loads during standing treadmill cycling. *Journal of Applied Biomechanics, 9*, 202-218.
Sanderson DJ (1991). The influence of cadence and power output on the biomechanics of force application during steady-rate cycling in competitive and recreational cyclists. *Journal of Sports Sciences, 9*, 131-203.
Sanderson DJ, Henning EM, Black AH (2000). The influence of cadence and power output on force application and in shoe pressure distribution during cycling by competitive and recreational cyclists. *Journal of Sports Sciences, 18*, 173-181.

* cited by examiner

*Primary Examiner*—Manuel L Barbee

(57) ABSTRACT

A power meter for power a pedal and crank arm based drive mechanism measures and displays athletic performance information as a measure of a physical quantity, power, using a flexible force sensor inserted into a cycling shoe. Mathematical cycling models and data from the flexible force sensor are used to calculate the power.

12 Claims, 10 Drawing Sheets

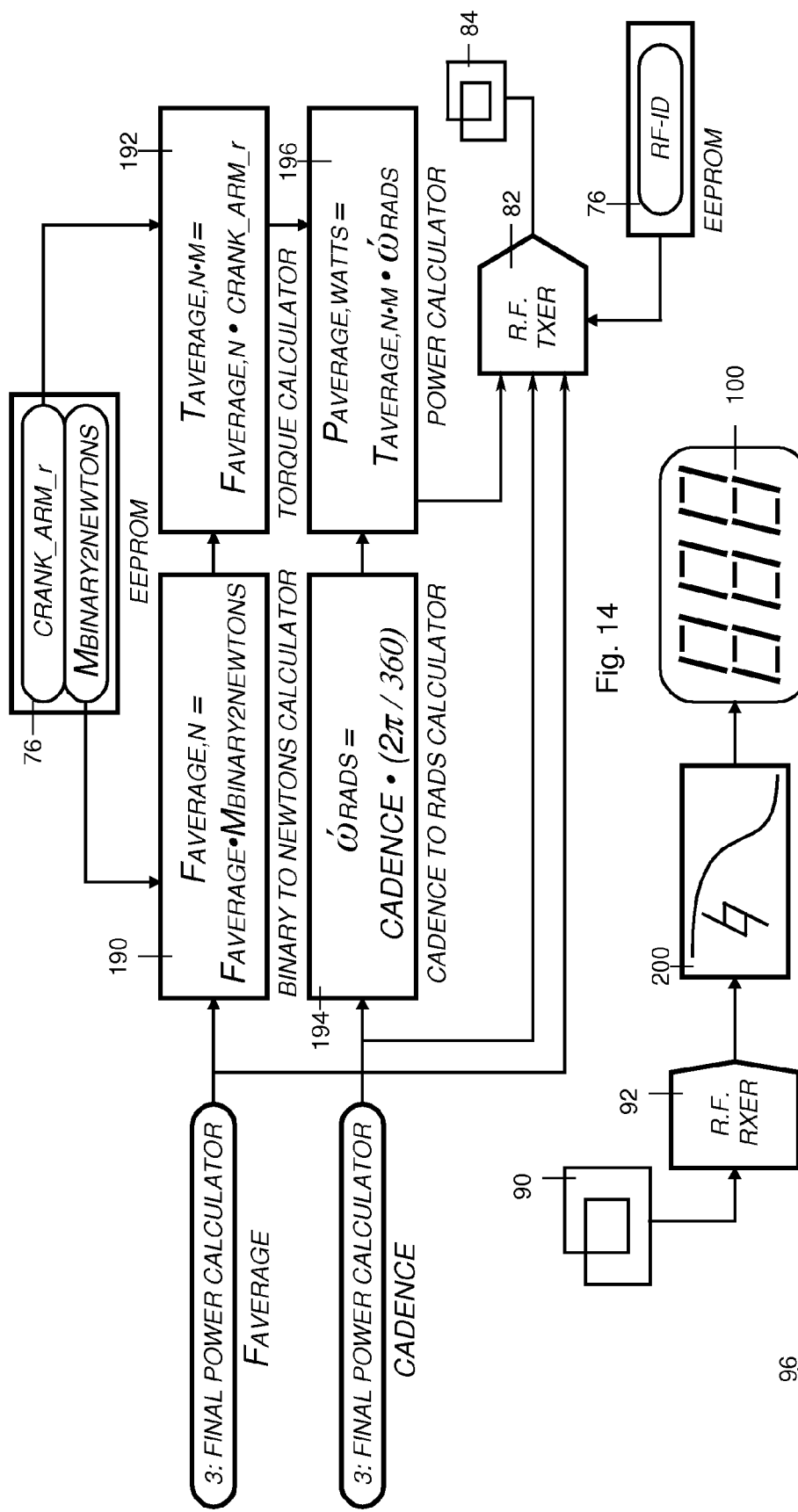

PORTABLE POWER METER FOR CALCULATING POWER APPLIED TO A PEDAL AND CRANK ARM BASED DRIVE MECHANISM AND A METHOD OF CALCULATING THE POWER

CROSS-REFERENCE TO RELATED APPLICATIONS

This is the first application filed for the present invention.

FIELD OF THE INVENTION

The present invention relates in general to the measurement of athletic performance and, in particular, to measuring the athletic performance of a cyclist using a portable power meter and a force sensor inside of a cycling shoe worn by the cyclist.

BACKGROUND OF THE INVENTION

Athletic performance information is of interest to most participants in sport. Athletic performance is commonly measured as a factor of time or speed. However, not all sports are well suited for using such factors as a measure of performance. For example, cycling performance is strongly influenced by environmental factors. Because a distance cycled is significantly influenced by conditions such as such as wind, riding surface and gradient, speed and time measurements may not accurately reflect a cyclist's performance.

It is has been established by scientific research that pedaling patterns amongst cyclists are stereotypical and that a lack of freedom in a biomechanical interface with a pedal and crank arm drive mechanism of a bicycle causes all cyclists to apply force in the same general manner. It is has also been established by scientific research that most cyclists apply substantially the same power to a pedal and crank mechanism with each leg. Consequently, the way in which an applied force is related to the power that propels the pedal and crank arm mechanism is likewise stereotypical, and measuring a representative proportion of the applied force should permit propulsive power to be calculated to an acceptable degree of accuracy. If propulsive power could be accurately calculated, a truer gauge of athletic performance could be achieved.

SUMMARY OF THE INVENTION

It is therefore an object of the invention to provide a portable power meter for calculating power applied to a pedal and crank arm based drive mechanism, and a method of calculating the power.

The invention therefore provides a power meter for calculating power applied to a pedal and crank arm based drive mechanism, comprising: a flexible force sensor inside a shoe worn by a person applying force to a pedal of the pedal and crank arm based drive mechanism, the flexible force sensor being placed within the shoe so that at least a representative proportion of a total force applied by the person to the pedal and crank arm based drive mechanism is sensed; and a processor for receiving force signals from the force sensor and for using the force signals in mathematical models to calculate the power.

The invention further provides a method of calculating power applied to a pedal and crank arm based drive mechanism, comprising: receiving force signals from a flexible force sensor inside a shoe worn by a person applying force to the pedal and crank arm based drive mechanism, the flexible force sensor being placed within the shoe so that at least a representative proportion of a total force applied by the person is sensed; and using the force signals in mathematical models to calculate the power.

BRIEF DESCRIPTION OF THE DRAWINGS

Further features and advantages of the present invention will become apparent from the following detailed description, taken in combination with the appended drawings, in which:

FIG. 14 is a flow diagram illustrating a third stage of processing the signals output by the force sensor; and FIG. 15 a flow diagram illustrating a final stage of processing the signals output by the force sensor.

DETAILED DESCRIPTION OF THE PREFERRED EMBODIMENT

The invention provides a power meter for measuring a physical quantity, power, applied to a pedal and crank arm based drive mechanism by a person applying force to the mechanism. The power meter includes a force sensor placed between a sole of the person's foot and an inside sole of the person's shoe. As the person pedals, at least a representative proportion of a normal component of a force applied by the person's foot to the drive mechanism is sensed by the force sensor. Since the crank arm based drive mechanism defines a rotational apparatus, the force sensed is represented by a periodic curve. Using signal analysis techniques, a period of the crank arm's rotation can be determined and used to derive its angular velocity. Further, applying information derived from typical force vs. crank arm angular displacement curves, initial conditions can be predicted and crank arm displacement determined throughout a crank arm rotation. Using force vector and pedal angles described in cycling literature, a total force applied by the person is calculated from measured force, and from the total force applied, a force tangent to the crank arm is calculated. Crank arm torque is a product of tangent force and a distance to its application, and, power is a product of torque and angular velocity. In one embodiment, a power meter in accordance with the invention is portable from one crank arm based drive mechanism to another and is compatible with any pedal system, including latching cleat-based (clipless) pedal systems.

Figure 1:
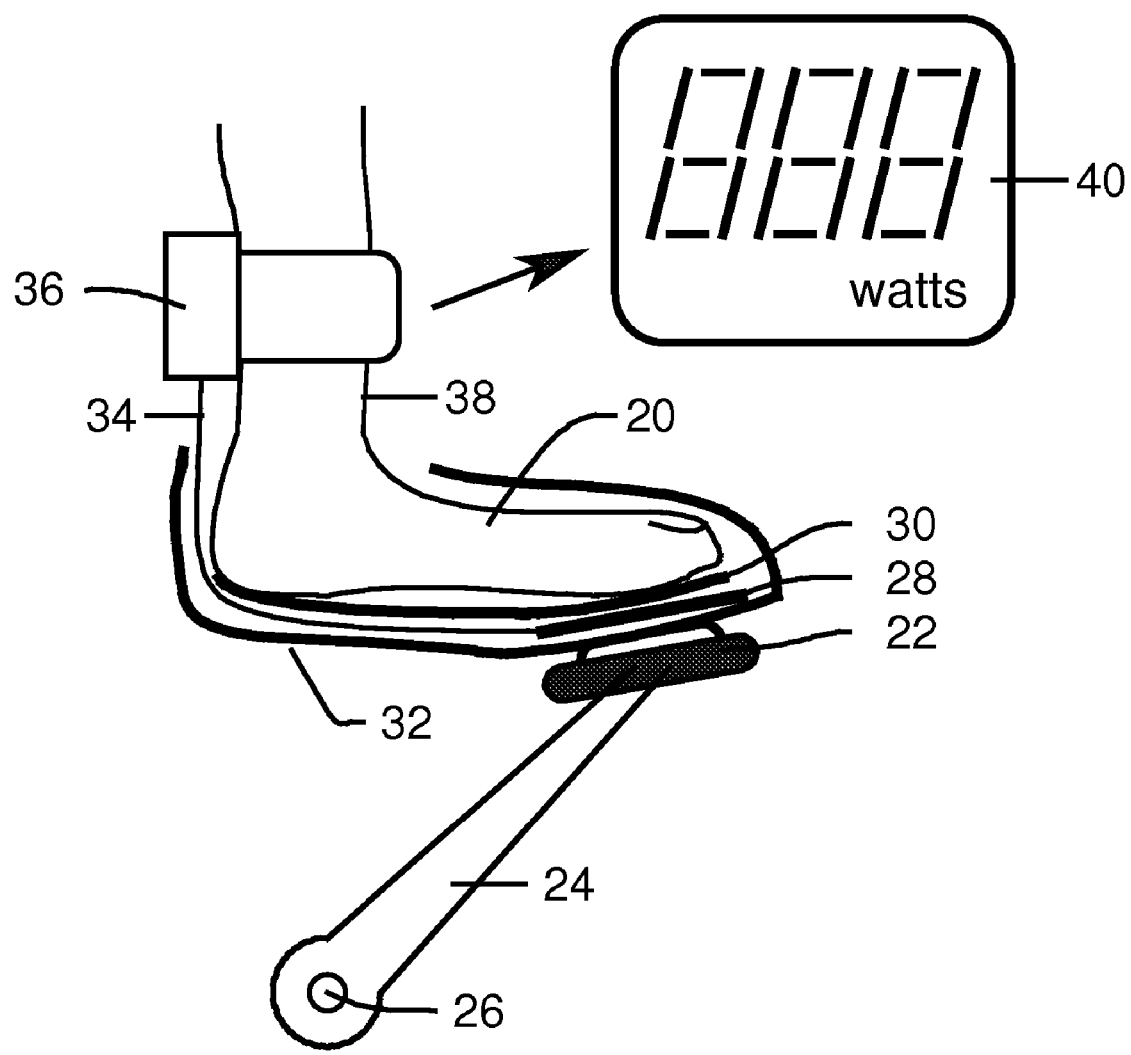
FIG. 1 is a schematic diagram of a pedal and crank arm drive mechanism of a bicycle illustrating how an embodiment of the invention may be implemented using a force sensor placed inside a cyclist's shoe.

FIG. 1 is a schematic diagram of a portion of a crank arm based drive mechanism. Force exerted by the person, hereinafter referred to as a cyclist, is exerted by the cyclist's foot 20 applied to a pedal assembly 22, which results in torque at crank arm 24 that causes rotation about crank arm shaft 26. A flexible force sensor 28, hereinafter referred to interchangeably as force sensor 28, is affixed to an insole 30 of a shoe worn by the cyclist, so that at least a representative proportion of a total force applied to the pedal assembly 22 by the cyclist's foot 20 is sensed by the force sensor 28 before it is applied to a sole of cycling shoe 32. A wire interface 34 runs under the insole 30 to an electronics unit 36. As shown, in one embodiment the electronics unit 36 is strapped to an ankle 38 of the cyclist. Alternatively, the electronics unit 36 may be: clipped to the cycling shoe 32; mounted under or embedded inside the insole 30; mounted inside the sole or an upper of the cycling shoe 32; or, in any other location that will not affect normal cycling. A second electronics unit 40 provides a user interface for accepting user input and displaying computed information of interest to the cyclist. The second electronics unit may be: mounted on the bicycle's handlebars; the bicycle's stem; worn as a wristwatch by the cyclist; mounted to a bicycle helmet; or, mounted in any other location that permits a cyclist to view the information.

The first electronics unit 36 and the second electronics unit 40 are interconnected by a data interface that does not interfere with the application of power to the pedal and crank arm based drive mechanism, i.e. does not interfere with cycling. In one embodiment, the data interface comprises a radio frequency data channel, as will be explained below with reference to FIGS. 3 and 4.

As explained above, most cyclists apply substantially the same force to the pedal and crank arm based drive mechanism with each leg. Consequently, in one embodiment of a power meter in accordance with the invention only one force sensor is used to measure force applied to the pedal and crank arm based drive mechanism. As will be further understood by those skilled in the art, force sensor 28, wire interface 34 and electronics unit 36 are inherently portable from crank arm based drive mechanism machine to another. It should be noted that measured force is proportional to calculated power in a predetermined ratio dependent on the type of propelled machine. Consequently, the power meter in accordance with the invention will not necessarily accurately calculate power if transported between different types of machine, from an upright to a recumbent bicycle, for example. However, the power meter can be expected to accurately calculate power when transported between machines of the same type, one upright bicycle to another for example. Electronics unit 40 can be packaged so that it is also easily removed from one machine and installed on another, or packaged in a wristwatch or helmet-attachable configuration that transports as easily as the electronics unit 36.

Figure 2:
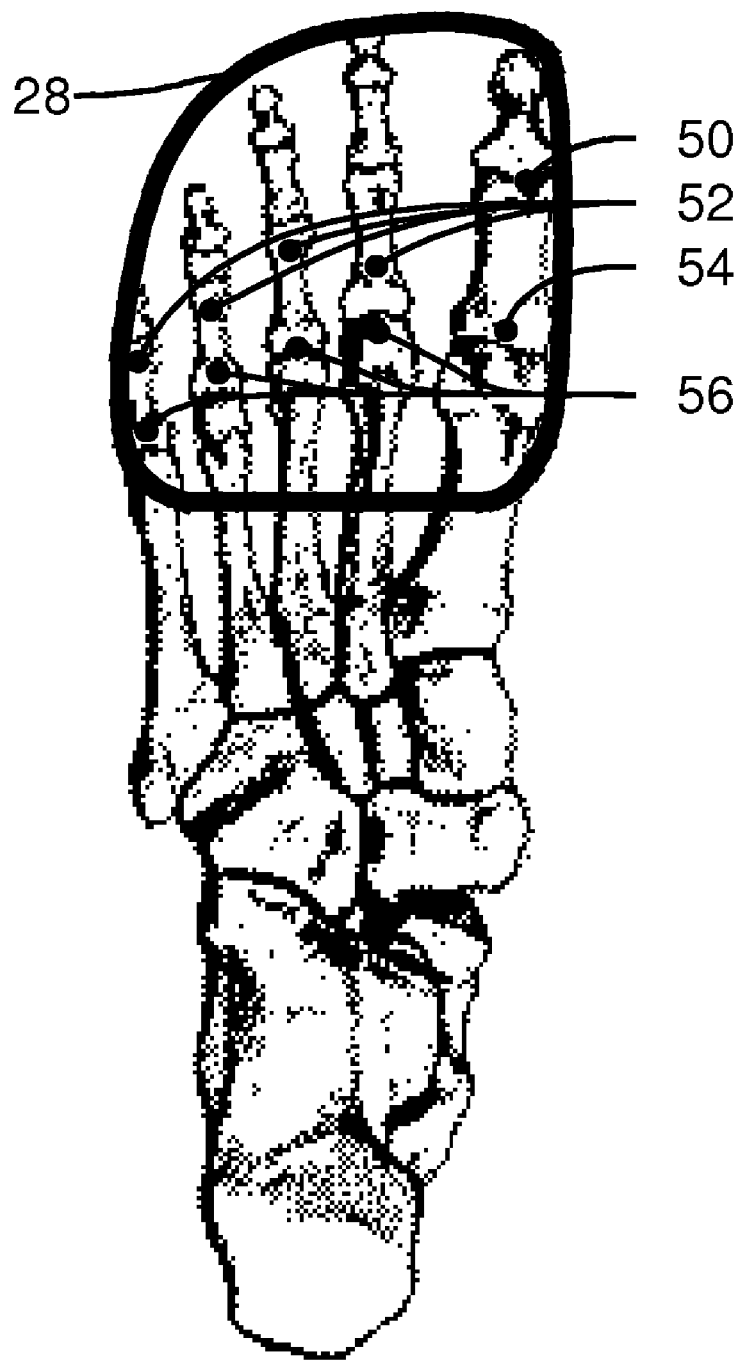
FIG. 2 is a schematic diagram of a skeletal foot illustrating the force sensor shown in FIG. 1, designed to detect forces applied by primary loading structures of the foot during cycling.

FIG. 2 is a bottom plan view of force sensor 28 shown in outline in front of a foot skeleton. In accordance with one embodiment of the invention, the force sensor 28 is a custom made Flexiforce® sensor manufactured by Tekscan of South Boston, Mass., USA. It is known that primary loading structures of the foot/pedal interface are, in order of relevance, the 1st metatarsal head 54 and hallux 50, metatarsal heads 2-5 indicated at 56 and toes 2-5 indicated at 52. The remainder of the foot makes a much smaller contribution to the application of force. In one embodiment of the invention, the force sensor 28 only captures forces applied by these primary loading structures of the foot.

Figure 3:
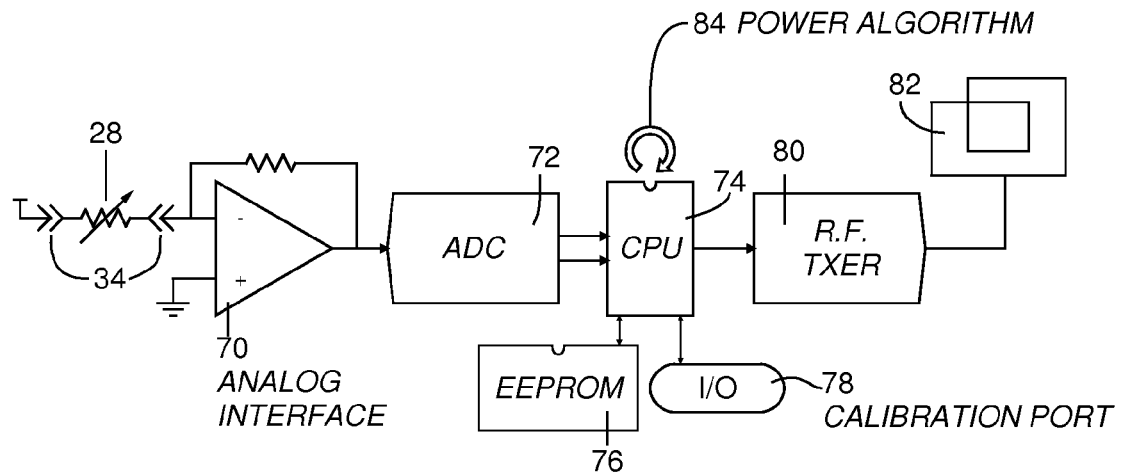
FIG. 3 is a block diagram of an electronics unit connected to the force sensor shown in FIG. 1.

FIG. 3 is a block diagram showing functional components of the electronics unit 36. Force sensor 28 is connected via wire interface 34. If a Flexiforce® sensor is used, its conductance is linear with force, and an analog interface 70 is used to generate an output voltage that is linear with the applied force. Other analog interfaces may not generate an output voltage that is linear with force, but they will generate a voltage that has a predetermined relationship to a force sensed by the force sensor. The analog interface 70 may contain a variable reference circuit for adjusting a range of the output voltage, depending on whether the cyclist is seated or standing, as will be explained below in more detail. The voltage output by the analog interface 70 drives an analog-to-digital converter 72, which is controlled by a central processing unit (CPU) 74 and sampled at a known and constant rate. The CPU 74 may be, for example, a microprocessor or a digital signal processor. The CPU 74 is responsible for executing a power algorithm 84 that calculates the cyclist's power based on force sensed by the force sensor 28. Data resulting from the calculation is transmitted to the electronics unit 40 (see FIG. 1) by a radio frequency transmitter 80 and antenna 82 via a data channel. During calibration mode, calibration port 78 is used to interface to electronics unit 40. EEPROM memory 76 stores data generated during calibration. Operating power is supplied, for example, by a battery driven power supply, which is not shown but is very well known in the art.

Figure 4:
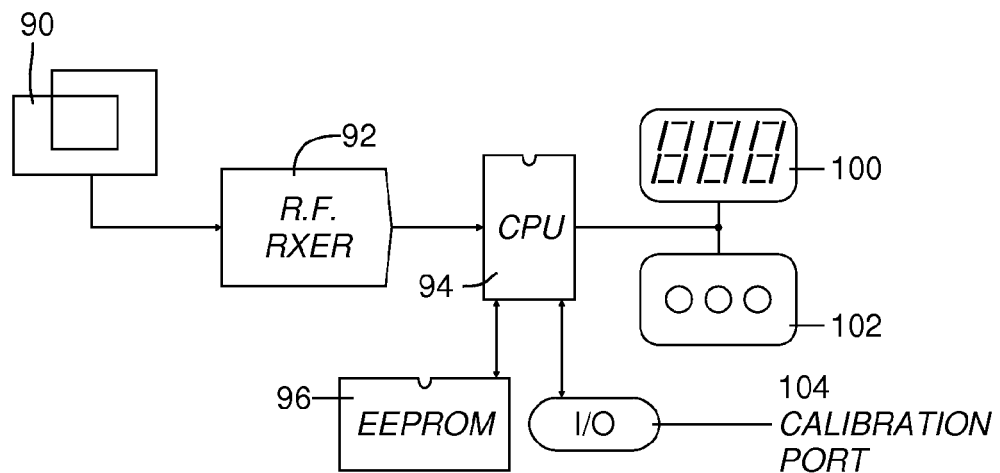
FIG. 4 is a block diagram of an electronics unit used to present a visual display to the cyclist.

FIG. 4 is a block diagram showing functional components of the electronics unit 40. An antenna 90 and a radio frequency receiver 92 receive data transmitted via the data channel by the electronics unit 36. A CPU 94 controls the user interface, which includes a display 100 and switches 102. Calibration data and user data are stored in EEPROM memory 96. During calibration mode, calibration port 104 is used to interface to electronics unit 36. Operating power for electronics unit 40 is supplied, for example, by a battery driven power supply, which is not shown but is very well known in the art.

The Power Algorithm

For a rotational system such as the crank arm and pedal drive train found on a bicycle, rotational power is defined as:

$$P = T \cdot \omega \qquad \text{Eq.1}$$

where: P=power; T=crank arm torque; and, $\omega$=crank arm angular velocity.

In the power algorithm 84, $\omega$ is assumed to be constant for one crank arm rotation. As the force function is periodic, its period ($\Delta t$) can be determined from frequency or time domain signal analysis. For one period $\Delta \omega$ is $2\pi$ or 360°. This gives:

$$\omega = \Delta \omega / \Delta t \qquad \text{Eq.2}$$

Torque is defined as:

$$T = F_{EFFECTIVE} \cdot r \quad \text{Eq.3}$$

where: $F_{EFFECTIVE}$=force tangent to the crank arm; and, r=distance from $F_{EFFECTIVE}$ to a center of rotation.

$F_{EFFECTIVE}$ is the portion of the total applied force that is tangent to the crank arm:

$$F_{EFFECTIVE} = F_{CYCLIST} * \cos \Theta \quad \text{Eq.4}$$

where: $F_{CYCLIST}$=magnitude of the force from the cyclist; and, $\Theta$=the angle of the applied force with respect to the crank arm.

Force sensor 28 measures forces normal to the pedal. Thus:

$$F_{CYCLIST} = F_{PEDAL} / \cos \phi \quad \text{Eq.5}$$

where: $F_{PEDAL}$ is the force measured by the sensor 28; and, $\phi$=the angle of applied force with respect to the pedal.

During the up-stroke $\Theta/\phi$ combinations can result in negative effective forces and are referred to as "$F_{NEGATIVE}$". As is understood by those skilled in the art, these negative forces can contribute significantly to the overall power output during low power cycling. Although common cycling lore suggests that cyclists "pull-up" during the up-stroke, creating a positive torque throughout the entire crank arm rotation scientific literature indicates that this is not the case.

Figure 5:
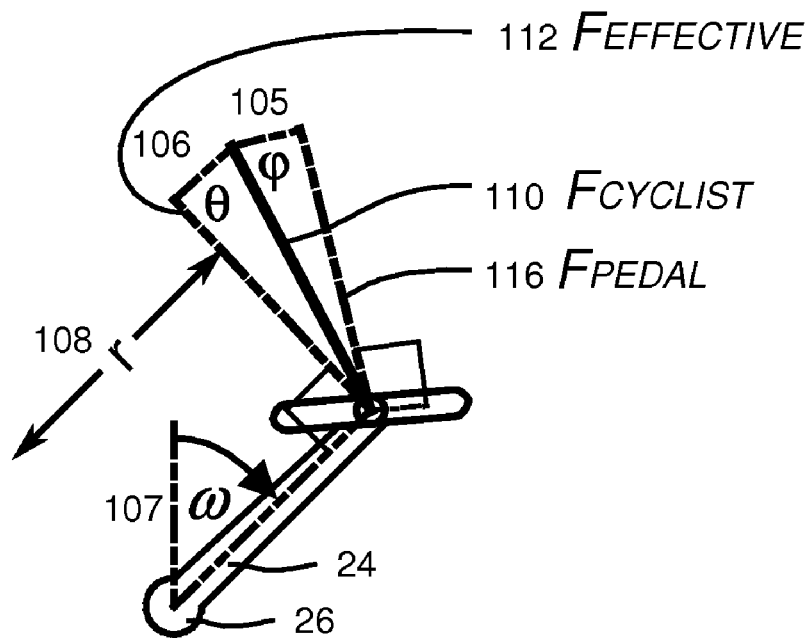
FIG. 5 is a schematic diagram of a bicycle pedal showing force vectors and angles when an applied force propels the bicycle.
Figure 6:
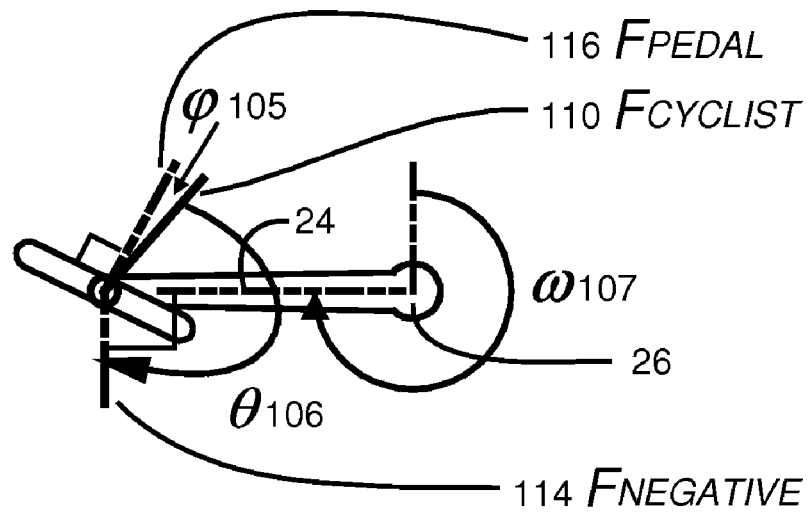
FIG. 6 is a schematic diagram of the bicycle pedal showing force vectors and angles when an applied force retards propulsion of the bicycle.

FIG. 5 and FIG. 6 schematically illustrate a trigonometry of the force vectors. FIG. 5 illustrates the geometric relationships between these force vectors during a typical down-stroke condition ($\omega$ 107≈45°); and, FIG. 6 illustrates the geometric relationship during an up-stroke condition ($\omega$ 107≈270°). $F_{PEDAL}$ 116, as measured by force sensor 28, is related to the total output force from the cyclist $F_{CYCLIST}$ 110 by the cosine of angle $\phi$ 105 as described above in Eq.5. $F_{EFFECTIVE}$ 112 or $F_{NEGATIVE}$ 114, the forces that cause torque in crank arm 24 about crank arm shaft 26, are related to $F_{CYCLIST}$ 110 by the cosine of angle $\theta$ 106 as described above in Eq.4.

Differences between three cycling conditions a) seated flat, b) seated climbing, and c) standing climbing have been studied and reported in scientific literature. The differences between the seated flat and seated climbing conditions were determined to be small, but the differences between standing cycling and seated cycling were determined to be significant. A magnitude of the peak forces are much higher during standing cycling, but more importantly, the crank arm rotation angle at which this peak force occurs was determined to be different. For seated flat cycling, the peak force occurs at $\omega$≈107°, for seated climbing, the peak occurs at $\omega$≈101°. For standing cycling, the peak force occurs at $\omega$≈155°.

Seated flat conditions generally involve cadences >~75 RPM and seated climbing conditions generally involve cadences <~75 RPM. As such, the power algorithm 84 can determine seated flat vs. seated climbing based on cadence. To avoid a "step function" at 75 RPM an average of each condition can be used around this switching cadence.

There are at least two methods to determine seated vs. standing cycling. One known method is to link peak force during standing conditions to body weight. If the peak force exceeds a predetermined percent of the cyclist's weight, the cyclist is known to be standing. Alternately, during standing cycling the crank arm angular displacement at which the force peaks occur is later for standing cycling, as explained above. This can be used in the power algorithm 84 to determine whether the cyclist is seated or standing. In one embodiment of the invention, if the crank arm rotation difference between maximum and minimum power is greater than a predetermined threshold (170° for example), the cyclist is seated, otherwise, the cyclist is standing.

Figure 7:
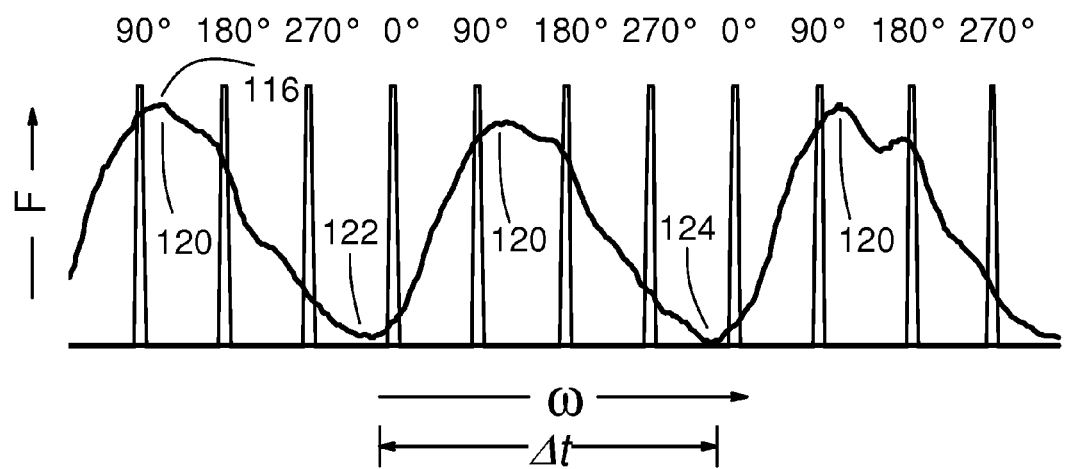
FIG. 7 is a graphical representation of a typical profile of a measured force signal that is normal to a bicycle pedal during seated cycling.

FIG. 7 is a graphical representation of a signal for $F_{PEDAL}$ 116 for seated cycling that has been digitized and sampled. A complete crank arm rotation is found between minima force conditions 122 and 124. Peak force conditions 120 are used to determine coo: as described above $\omega_0$≈101°-107°, depending on rotation cadence.

Figure 8:
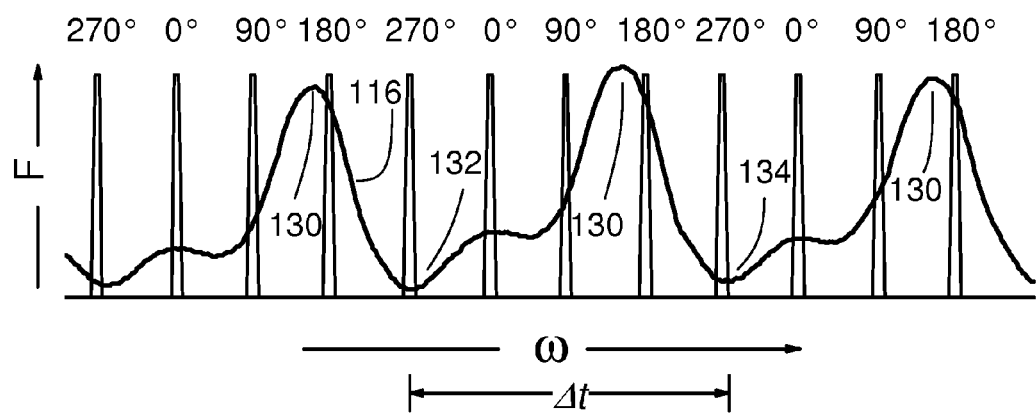
FIG. 8 is a graphical representation of a typical profile of a measured force signal that is normal to a bicycle pedal during standing cycling.

FIG. 8 is a graphical representation of a signal for $F_{PEDAL}$ 116 for standing cycling. A complete crank arm rotation is found between minima force conditions 132 and 134. Peak force conditions 130 are used to determine $\omega_0$: as described above $\omega_0$≈155°.

Figure 9:
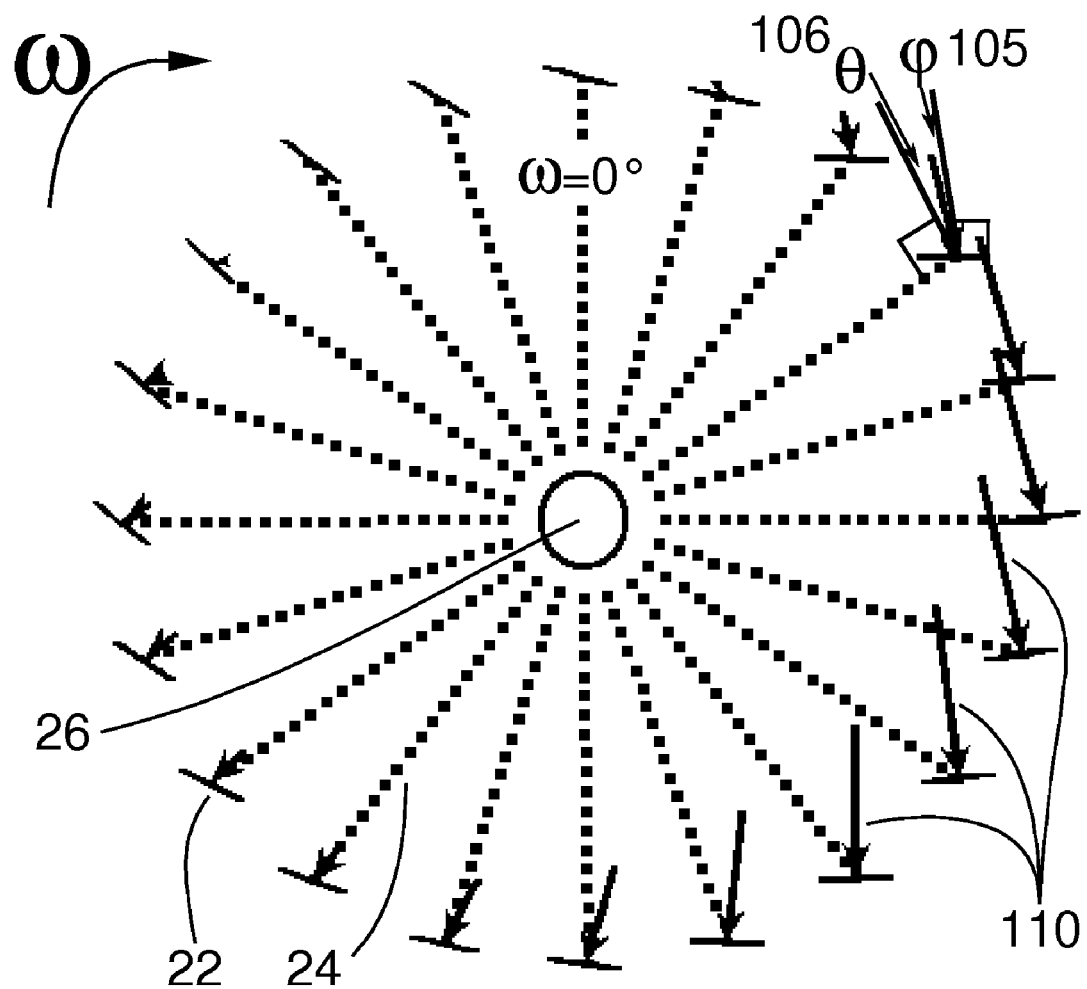
FIG. 9 is a 'clock diagram', which is a geometric representation of cycling components and forces throughout one rotation of a bicycle crank arm.

For each of FIG. 8 and FIG. 9, At can be determined using force minima, 120, 130 respectively (as both the number of samples and the sample rate are known by the CPU 74). Crank arm angular velocity can be determined using Eq.2. Consequently, all the parameters required to determine crank arm displacement for each sample of $F_{PEDAL}$ are known:

$$\omega = \omega_0 + \dot{\omega} t \quad \text{Eq.6}$$

FIG. 9 is a 'clock diagram' that is known in the art and popular in cycling literature. The crank arm 24, pedal 22 and the force vector from the cyclist (Fcyclist) 110 are shown in their correct geometric configuration for various positions of crank arm rotation ($\omega$). This clock diagram can be used to determine $\phi$ 105 and $\Theta$ 106 for each angle $\omega$ in a crank arm rotation. The clock diagram has been found to be similar for both elite athletes, and recreational cyclists. The model shown in FIG. 9 is appropriate for seated flat cycling.

The effects of cadence on pedaling efficiency for both elite and recreational athletes have also been described in scientific literature. It was determined that during slow cadence conditions (such as exist during seated hill climbing) the bottom part of pedal cycle is more effective. A prior art clock diagram for seated climbing can be used to determine $\phi$ and $\Theta$ angles for the power algorithm 84. A clock diagram for standing cycling has not been located in the published literature. However, normal and tangential forces and pedal angles throughout a crank arm rotation during standing cycling have been published, and these are used in combination to determine $\phi$ and $\Theta$ angles for standing cycling.

The scientific literature demonstrates low statistical variance among studied subjects, regardless of athletic conditioning and other factors. As explained above, it is suggested that the limited freedom afforded by the biomechanical interface to the bicycle results in all cyclists pedaling in a stereotypical pattern. The consequence of this repeatability indicates that using tables to determine $\phi$ and $\Theta$ throughout a crank arm's rotation will yield to accurate results in the calculation of $F_{EFFECTIVE}$ and $F_{NEGATIVE}$.

For normal cadence seated cycling, one embodiment of the power algorithm 84 uses the following table for a $\omega$, $\phi$ and $\Theta$ model:

TABLE 1

Normal Cadence Cycling Angles

ω @ Peak Force: 107°

| ω (°) | 0 | 18 | 36 | 54 | 72 | 90 | 108 | 126 | 144 | 162 | 180 | 198 | 216 | 234 | 252 | 270 | 288 | 306 | 324 | 342 |
|---|---|---|---|---|---|---|---|---|---|---|---|---|---|---|---|---|---|---|---|---|
| φ (°) | 30 | 26 | 17 | 15 | 12 | 6 | 3 | 0 | 0 | 5 | 8 | 12 | 12 | 12 | 12 | 16 | 16 | 44 | 36 | 30 |
| θ (°) | 74 | 56 | 39 | 23 | 2 | 15 | 26 | 42 | 56 | 66 | 74 | 78 | 90 | 104 | 112 | 134 | 145 | 180 | 140 | 120 |

For slow cadence seated cycling, one embodiment uses the following table for the ω, φ and Θ model:

TABLE 2

Slow Cadence Cycling Angles

ω @ Peak Force: 101°

| ω (°) | 0 | 18 | 36 | 54 | 72 | 90 | 108 | 126 | 144 | 162 | 180 | 198 | 216 | 234 | 252 | 270 | 288 | 306 | 324 | 342 |
|---|---|---|---|---|---|---|---|---|---|---|---|---|---|---|---|---|---|---|---|---|
| φ (°) | 20 | 16 | 14 | 12 | 11 | 6 | 7 | 5 | 0 | 0 | 7 | 18 | 28 | 52 | 36 | 28 | 20 | 20 | 20 | 20 |
| θ (°) | 90 | 63 | 38 | 24 | 3 | 15 | 25 | 48 | 55 | 67 | 70 | 67 | 63 | 58 | 80 | 114 | 142 | 180 | 142 | 114 |

For standing cycling, one embodiment uses the following table for the ω, φ and Θ model:

TABLE 3

Standing Cycling Angles

ω @ Peak Force: 155°

| ω (°) | 0 | 30 | 60 | 90 | 120 | 150 | 180 | 210 | 240 | 270 | 300 | 330 |
|---|---|---|---|---|---|---|---|---|---|---|---|---|
| φ (°) | 20 | 16 | 5 | 2 | 0 | 3 | 3 | 3 | 6 | 6 | 16 | 20 |
| θ (°) | 90 | 62 | 32 | 3 | 33 | 53 | 75 | 98 | 112 | 140 | 140 | 110 |

Figure 10:
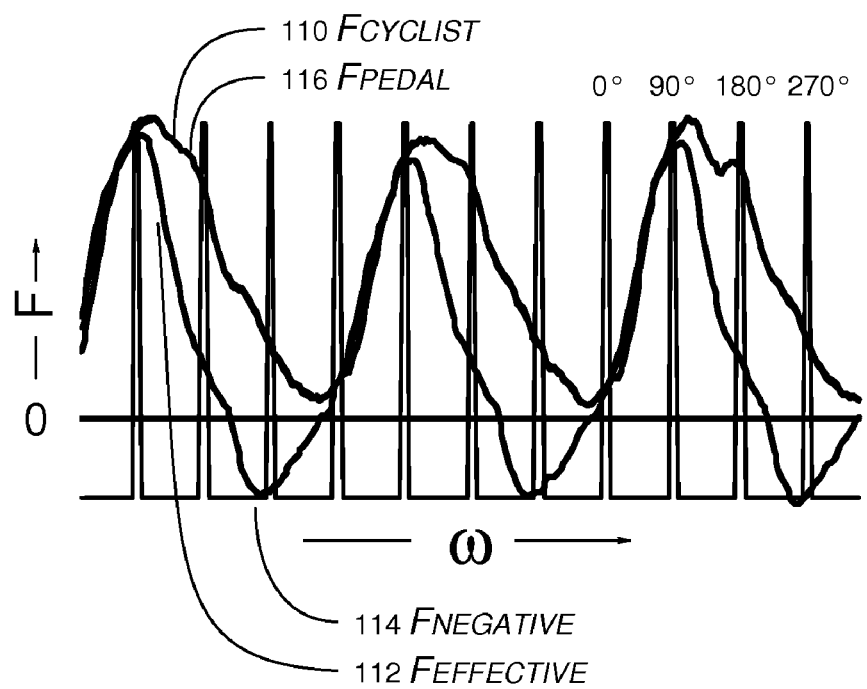
FIG. 10 is a graphical illustration of effective forces calculated from measured pedal forces using angles predicted by the clock diagram for seated cycling shown in FIG. 9.

FIG. 10 is a graphical representation of the resultant $F_{CYCLIST}$ 110 and $F_{EFFECTIVE}$ 112/$F_{NEGATIVE}$ 114 calculated from $F_{PEDAL}$ 116 for normal cadence seated cycling, computed using Eq. 4 and Eq. 5 with φ and Θ derived from Table 1.

Figure 11:
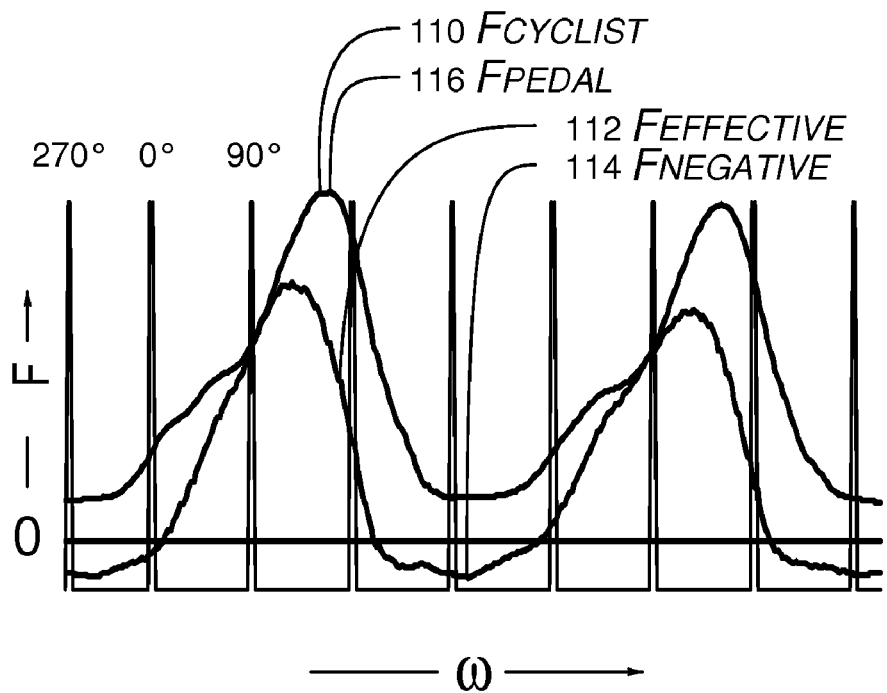
FIG. 11 is a graphical illustration of effective forces calculated from measured pedal forces using angles predicted by a clock diagram for standing cycling.

FIG. 11 is a graphical representation the resultant $F_{CYCLIST}$ 110 and $F_{EFFECTIVE}$ 112/$F_{NEGATIVE}$ 114 calculated from $F_{PEDAL}$ 116 for standing cycling, using Eq. 4 and Eq. 5 with φ and Θ derived from Table 3. Slow cadence cycling is represented by a graph similar to the one shown in FIG. 10.

$F_{EFFECTIVE}$ and $F_{NEGATIVE}$ are integrated during a crank arm rotation to obtain:

$$F_{AVERAGE} = 2 \cdot \{[\Sigma F_{EFFECTIVE} - \Sigma F_{NEGATIVE}]/n\} \quad \text{Eq. 7}$$

where: n=number of samples in the crank arm rotation period; and, $F_{AVERAGE}$=an average force that propelled the bicycle during that period. (Note: multiplying factor of 2 is required if only one of two pedals, i.e. one sensor 28 is used for analysis.)

Furthermore, since crank arm length r is constant, Eq. 3 can be written for one crank arm rotation:

$$T_{AVERAGE} = F_{AVERAGE} \cdot r \quad \text{Eq. 8}$$

where: r=the length of the crank arm from the crank arm shaft to pedal axis spindle.

Finally, for one crank arm rotation:

$$P_{AVERAGE} = T_{AVERAGE} \cdot \acute{\omega} \quad \text{Eq. 9}$$

Figure 12:
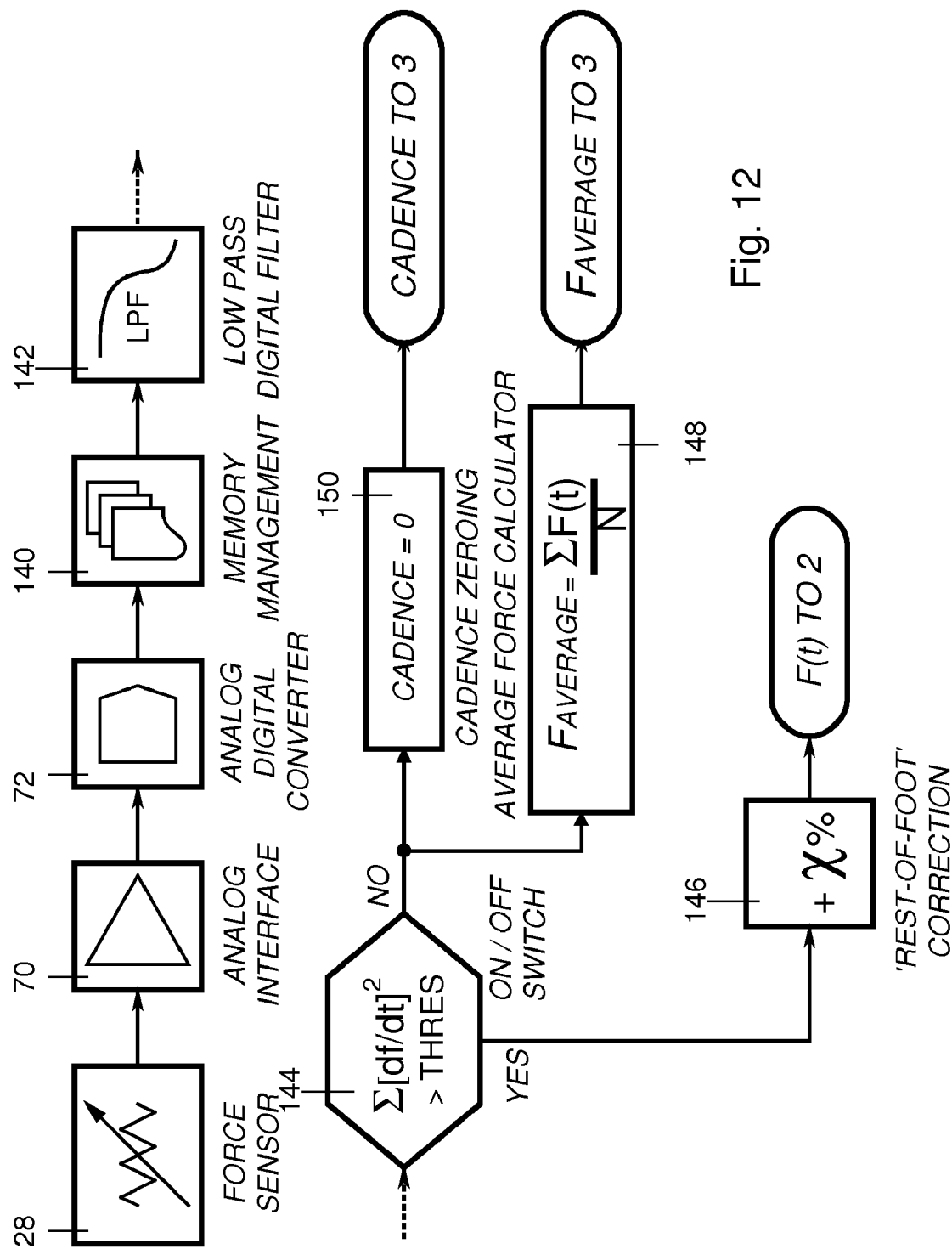
FIG. 12 is a flow diagram illustrating a first stage of processing signals output by the force sensor shown in FIG. 1.

FIG. 12 is a flow diagram illustrating a first stage of signal processing of the output from force sensor 28. Those skilled in the art will understand the tradeoffs required to suitably digitize any signal. The more samples per crank arm rotation, the greater the resolution of the integrator that performs Eq. 7. However, in order to use frequency analysis methods such as a Discrete Fourier Transform (DFT), a size of the data array must be long enough to contain at least one period of the slowest pedal cadence of interest. A high resolution increases the size of this array, which burdens processor speed and memory requirements. These in turn affect computational and storage capacity as well as power usage.

In one embodiment of the invention, a minimum cycling cadence is assumed to be 40 RPM, and a maximum cycling cadence is assumed to be 130 RPM. In that embodiment, a 6.25 ms sampling rate is used. This permits, at 120 RPM cycling, ~80 samples per integration, and at 40 RPM cycling, ~240 samples are stored per rotation.

A memory management unit 140 sorts data into 256 sample buffers (not shown). As it is improbable that the sample buffer's boundaries will align with crank arm rotation boundaries, a circular array is used and each newer 256 samples are 'stitched' to a previous 256 samples to form a 512 sample buffer. At 40 RPM, two full crank arm rotations are contained in a buffer of this size. An index to a last cycle is also treated as circular so that no crank arm rotations are lost. Optionally, memory management unit 140 can also store data for later use, such as transmission to a personal computer for force analysis.

Low pass filter 142 performs digital filtering. In one embodiment the low pass filter 142 is an equal weight smooth-filter with n=7.

The calculation performed by on/off switch 144 of an integral of a square of the derivative is, in mathematical terms, cyclist is seated, otherwise the cyclist is standing. If the cyclist is seated, a cadence model calculator 182 decides what percentages of the slow cadence $\omega$, $\phi$ and $\Theta$ model 176 or normal cadence $\omega$, $\phi$ and $\Theta$ model 174 effective force calculator 168 will use. Table 4 is used to determine those percentages:

TABLE 4

Normal vs. Slow Cadence Percentages ($\alpha/\epsilon$)

| | Cadence | | | | | | | | | | |
|---|---|---|---|---|---|---|---|---|---|---|---|
| | <65 | 66 | 67 | 68 | 69 | 70 | 71 | 72 | 73 | 74 | >75 |
| $\alpha$ | 100% | 90% | 80% | 70% | 60% | 50% | 40% | 30% | 20% | 10% | 0% |
| $\epsilon$ | 0% | 10% | 20% | 30% | 40% | 50% | 60% | 70% | 80% | 90% | 100% | the 'power' of a function. On/off switch 144 performs this operation on a digitized force signal $F_{PEDAL}$ 116 with representative samples as shown in FIGS 7 and 8 for seated and standing cycling, respectively. The result is compared to a threshold to determine whether further processing should continue. If no significant power is found in the input signal, the device is 'off' and it is assumed that the cyclist is coasting, the device is not in use, or, it is being calibrated using a steady state force. Cadence is set to zero in cadence zeroing unit 150, and $F_{AVERAGE}$ is calculated by average force calculator 148. $F_{AVERAGE}$ during the 'off' condition is defined as the average force over all samples. Both cadence and $F_{AVERAGE}$ are ready to be used by a final power calculator which is described below.

If it is determined by the on/off switch 144 that the device is 'on', it is assumed the cyclist is pedaling and processing of the force sensor's signal continues while a 'Rest-of-Foot' correction unit 146 adds any missing $\chi\%$ of force applied by the mid-foot and heal. In one embodiment $\chi$=13%, which is generally accepted as the proportion of applied pedal force contributed by the rest of the foot.

Figure 13:
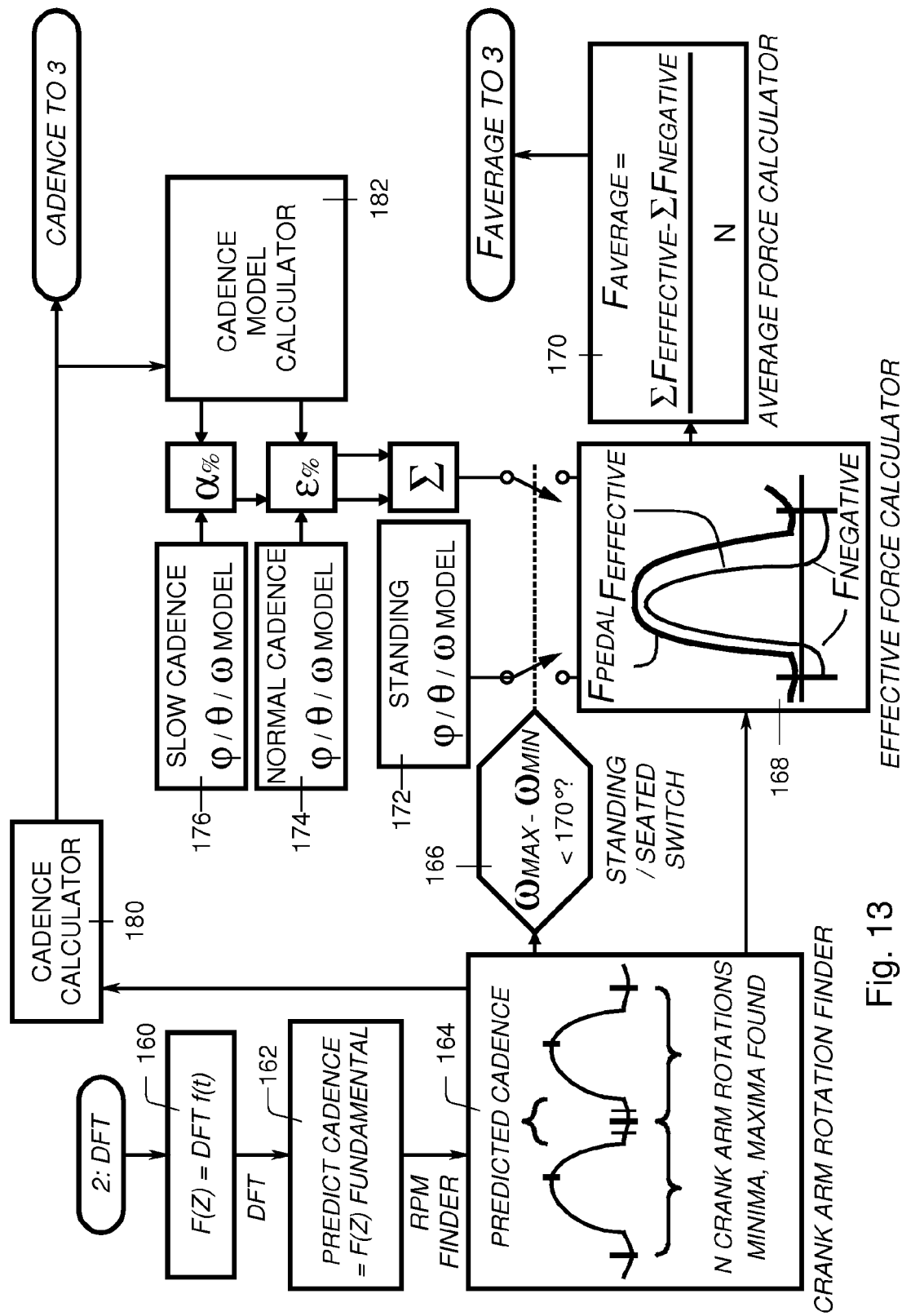
FIG. 13 is a flow diagram illustrating a second stage of processing the signals output by the force sensor.

FIG. 13 is a flow diagram illustrating a second stage of processing the signals output by the force sensor. A Discrete Fourier Transform unit 160 converts the signal to the frequency domain by performing the FFT of the signal. The 512 sample array is down-sampled by a factor of 2 to 256 samples, windowed using a trapezoidal function, and then zero-padded to 1024 points which permits a first approximation for cadence to a resolution of ~5 RPM. An RPM finder 162 determines a fundamental frequency of the force signal. If a cadence inside the valid range is determined, signal processing continues in the time domain.

Crank arm rotation finder 164 determines actual crank arm rotation periods by searching for local minima in a range predicted by the FFT. If local minima are found, the results of the FFT are considered valid and it is assumed a valid crank arm rotation was found between minima. Maximum force conditions for the pedal cycle are determined by locating a peak between the minima. A cadence calculator 180 determines exact cadence from these minima and value(s) for each period are ready to be transmitted for display by electronics unit 40, and used by the final power calculator described below with reference to FIG. 14. Optionally, cadence data can be stored for later use such as transmission to a personal computer.

A standing/seated switch 166 compares the crank arm angle where peak and minimum forces occurred. In one embodiment of the invention, if the difference is greater than the predetermined threshold (170° for example), then the If the cyclist is found to be standing, a standing cycling $\omega$, $\phi$ and $\Theta$ model 172 is used.

Effective force calculator 168 calculates effective force and negative effective force for each crank arm rotation. The initial condition for $\omega_0$ is set at the peak force sample, and $\omega$ is calculated for each sample using Eq. 2, $\phi$ and $\Theta$ are determined from look-up tables for each sample of $\omega$, after which Eq. 4 and Eq. 5 are performed for each sample for the entire crank arm rotation(s).

An average force calculator 170 performs Eq. 7 for the crank arm's rotation(s), and $F_{AVERAGE}$ value(s) are ready to be used by the final power calculator described below with reference to FIG. 14. Optionally, $F_{AVERAGE}$ may be stored for later use, such as transmission to a personal computer.

FIG. 14 is a flow diagram illustrating a final stage of the power calculation in accordance with the invention. In one embodiment of the invention, a binary-to-Newtons calculator 190 converts each $F_{AVERAGE}$ to manufacturer selected power units by multiplying $F_{AVERAGE}$ by a predetermined value, $M_{BINARY2NEWTONS}$. The selected power units may be metric or imperial units. $M_{BINARY2NEWTONS}$ is determined by the manufacturer for each force sensor using equation 10.

$$M_{BINARY2NEWTONS} = (\text{Known\_Force}_{NEWTONS})/A\_TO\_D\_\text{Output}_{BINARY} \quad \text{Eq.10}$$

where: Known_Force$_{NEWTONS}$ is a predetermined force applied to the selected force sensor, and A_TO_D_Output$_{BINARY}$ is a binary output of the analog-to-digital converter 72 when the predetermined force is applied.

After $M_{BINARY2NEWTONS}$ is determined, the power meter is put into calibration mode and the value of $M_{BINARY2NEWTONS}$ is stored in EEPROM memory 76 of electronic unit 36.

$T_{AVERAGE}$ is calculated in torque calculator 192 that performs Eq. 8. Torque calculator 192 requires input from EEPROM 76 for the radius of crank arm 24, set during calibration mode. Cadence-to-RADs calculator 194 converts cadence in RPM to cadence in RADs per second by multiplying Cadence$_{RPM}$ by $2\pi/360$. $P_{AVERAGE}$ is calculated in power calculator 196, which performs Eq. 9 for each crank arm rotation. $P_{AVERAGE}$, along with Cadence and $F_{AVERAGE}$, are packetized with RF-ID and broadcast to radio frequency transmitter 82 and antenna 84. RF-ID is set during calibration mode and stored in EEPROM 76.

FIG. 15 schematically illustrates processing performed by the electronics unit 40. Antenna 90 and radio frequency receiver 92 receive the data packets transmitted from electronics unit 36. If the RF-ID in a received data packet matches the RF-ID in local EEPROM 96, the data is made available to the display averaging unit 200, which smoothes the data and uses hysteresis to decrease jitter in output on display 100.

During calibration mode, electronics unit 36 is connected to electronics unit 40 via calibration ports 78 and 104. Data is entered and stored in EEPROM 76. The data includes, for example, variables representing a crank arm radius of the pedal and crank arm drive mechanism, a user selected RF-ID, and $M_{BINARY}2_{NEWTONS}$.

Those skilled in the art will note that electronics unit 36 performs all frequently occurring or computationally intensive mathematical functions, such as the DFT, cosine calculations, digital filtering, differentiation and integration. Electronics unit 40 performs only display functions, which need only be performed, for example, once every 256 sample periods, as determined by the memory management unit 140. The CPU requirements for electronics unit 40 are therefore reduced.

Although the embodiment described above as an example of the invention has been described with reference to two electronics units that share the computational load, it should be understood that other equally workable solutions can be used to achieve the same purpose. For example, at least all of the following have been contemplated as alternatives to the embodiment described in detail above:

Modifications to Electronics Apparatus:
- the inventor contemplates an embodiment in which force sensor 28 and electronics unit 36 are duplicated for both cycling shoes so that force is measured for both pedals and both crank arms;
- the inventor contemplates an embodiment in which a proximity switch based cadence sensor is added. Those skilled in the art will understand that this commonly used system employs switch or sensor components mounted on the bicycle frame and one of the bicycle's crank arms;
- the inventor further contemplates an embodiment in which a proximity switch based speed sensor is added. Those skilled in the art will understand that this commonly used system employs switch or sensor components mounted on the bicycle frame and on one of the bicycle's wheels.

Electronics Unit 36:
- may be packaged such that it can be clipped to the cyclist's shoe;
- may be packaged such that it is part of a removable insole for a cyclist's shoe;
- may be packaged such that it is an integral part of a sole or an upper of the cyclist's shoe.

Modifications to electronics units 36 and 40:
The inventor contemplates an embodiment wherein the algorithm executed by electronics unit 36 is instead executed by electronics unit 40. In this embodiment the data from force sensor 28 is transmitted directly from electronics unit 36 to electronics unit 40 before processing is performed. The data from force sensor 28 can be transmitted in its native analog form or first digitized using an analog-to-digital converter. This embodiment may be of particular interest when both pedals are sensed because a negative force sensed at one pedal can be segregated from a positive force being applied to the other pedal;

The inventor contemplates an embodiment in which the ω, φ and Θ angles are optimized for mountain bicycles;

The inventor contemplates an embodiment in which the ω, φ and Θ angles are optimized for recumbent bicycles;

The inventor contemplates an embodiment in which the ω, φ and Θ angles are optimized for indoor exercise bicycles including upright, recumbent, and spinning machines;

The inventor contemplates an embodiment where the ω, φ and Θ angles are optimized for other pedal powered vehicles;

The inventor contemplates an embodiment in which calibration data is stored in electronics unit 40 and binary-to-Newton calculator 190, torque calculator 192, cadence-to-rads calculator 194 and power calculator 196 are provisioned in electronics unit 40;

The inventor contemplates an embodiment in which time domain signal processing, such as threshold crossing of the force signal (or a derivative of the force signal) is used to calculate the signal's period;

The inventor contemplates an embodiment in which a user's weight is used to determine seated vs. standing cycling using the maximum force values compared to the user's weight, in a manner known in the art;

The inventor contemplates an embodiment in which signal minima of the force sensor 28 are used to determine initial conditions for crank arm angular displacement;

The inventor contemplates an embodiment in which a proximity switch based cadence sensor is used to determine crank arm angular velocity;

The inventor contemplates an embodiment in which a proximity switch based cadence sensor is used to determine initial conditions for crank arm angular displacement;

The inventor contemplates an embodiment in which simplifications to the signal processing algorithm are introduced. Such simplifications may include, but are not limited too:
1) averaging the signal from force sensor 28 over time and multiplying the average by a pre-calculated (or empirically determined) number that is equivalent to the effects of the φ and Θ angles.
2) using only the per-cycle peak of the signal from force sensor 28 and multiplying this result by a pre-calculated (or empirically determined) number that equals the effects of φ and Θ angles and another number calculated (or experimentally determined) to equal the effects of the peak force signal only being applied for a small portion of the crank arm rotation. However, the scientific literature indicates that inexperienced cyclists create a larger peak impulse then experienced cyclists, suggesting that accurate results may not be obtained using this method.
3) signal processing during only a portion of the crank arm rotation; such as neglecting the negative forces. However, the scientific literature suggests that negative forces play an important role during low power cycling, suggesting that only approximate results may be obtained using this method.
4) simplifications to the φ and Θ angles, such as assuming φ is 0°;
5) assuming that the pedal is horizontal or nearly horizontal with respect to a plane of a surface that the bicycle is traveling upon.

The inventor contemplates an embodiment in which semi-permanent memory is used to log data, including:
1) short term data, such as individual samples during crank arm rotation;
2) long term data, such as effective power per crank arm rotation for an entire bicycle ride.

The inventor contemplates an embodiment in which a time measuring device such as electronic real time clock is provided and a calculation of average power over the duration of an entire bicycle ride is performed.

The inventor contemplates an embodiment in which memory and a compare algorithm are used to determine the peak power over the duration of an entire bicycle ride.

The inventor contemplates an embodiment in which information besides $F_{AVERAGE}$, $P_{AVERAGE}$ and Cadence is displayed to the cyclist. Other parameters that may be displayed include, but are not limited to, $F_{PEAK}$, $F_{EFFECTIVE}$, $F_{NEGATIVE}$, and $T_{AVERAGE}$. Further the invention includes the calculation of percentages calculated from those parameters, such as $F_{NEGATIVE}/F_{AVERAGE}$ and $F_{EFFECTIVE}/F_{AVERAGE}$ and $F_{AVERAGE}/F_{PEAK}$.

The inventor contemplates an embodiment in which analog interface 70 contains a variable gain amplifier and its output is calibrated to give a known voltage at a known force.

The inventor contemplates an embodiment in which analog interface 70 contains a variable gain amplifier that adjusts "on the fly" in particular, lowering the gain for standing cycling conditions.

The inventor contemplates an embodiment in which a small DC offset is subtracted from the force signal.

The scope of the invention is therefore intended to be limited solely by the scope of the appended claims.

I claim:

1. A method of calculating power applied to a pedal and crank arm based drive mechanism, comprising:
   receiving force signals from a flexible force sensor inside a shoe worn by a person applying force to the pedal and crank arm based drive mechanism, the flexible force sensor being placed within the shoe so that at least a representative proportion of a total force applied by the person is sensed;
   using the force signals in mathematical models to calculate the power
   calculating an integral of a square of a derivative of the signal received from the force sensor versus time, and comparing a result to a threshold to determine whether the crank arm based drive mechanism is being rotated or is at rest; and
   if the crank arm based drive mechanism is at rest, setting cadence to zero and calculating average force as an average of all force samples.

2. The method as claimed in claim 1 wherein if it is determined that the crank arm based drive mechanism is not at rest, performing a rest-of-foot correction by adding to the force signals an assumed proportion of applied force contributed by the rest of the foot of the person.

3. The method as claimed in claim 2 further comprising:
   performing a Fast Fourier Transform (FFT) to convert the force signals to a frequency domain;
   down-sampling the converted signals samples by a predetermined downsampling factor;
   windowing the samples using a trapezoidal function; and
   performing a first approximation of cadence to determine a fundamental frequency of the force signals.

4. The method as claimed in claim 3 further comprising:
   determining actual crank arm rotation periods by searching for local minima in a range predicted by the FFT, and if local minima are found, assuming the results of the FFT are valid and that a valid crank arm rotation was found between the local minima;
   locating a peak between the minima; and
   determining cadence using the minima.

5. The method as claimed in claim 4 further comprising:
   comparing a crank arm angle where the peak and the minima were located
   and if a difference is greater than a predetermined threshold, then assuming the person is seated; else
   assuming the person is standing.

6. The method as claimed in claim 5 wherein:
   if it is assumed that the person is seated, selecting one of a slow cadence model and a normal cadence model to be used in an effective force calculation; else
   selecting a standing cycling model to be used in the effective force calculation.

7. The method as claimed in claim 6 wherein:
   the effective force calculation comprises calculating $F_{EFFECTIVE}$ and $F_{NEGATIVE}$ from $F_{PEDAL}$, using:

$$F_{EFFECTIVE} = F_{CYCLIST} \cdot \cos\theta \qquad \text{Eq. 4}$$

where: $F_{CYCLIST}$=magnitude of the force applied by the person; and, $\theta$=the angle of the applied force with respect to the crank arm; and $$F_{CYCLIST} = F_{PEDAL}/\cos\phi \qquad \text{Eq. 5}$$

where: $F_{PEDAL}$ is the force measured by the flexible force sensor; and, $\phi$=the angle of applied force with respect to the pedal;
   wherein $\theta$ and $\phi$ are derived from one of a table for the slow cadence model, a table for the normal cadence model and a table for the standing cycling model.

8. The method as claimed in claim 7 further comprising:
   performing an average force calculation using:

$$F_{AVERAGE} = 2 \cdot \{ [\Sigma F_{EFFECTIVE} - \Sigma F_{NEGATIVE}]/n \} \qquad \text{Eq. 7}$$

where: n=number of samples in the crank arm rotation period; and, $F_{AVERAGE}$=an average force that propelled the pedal an crank arm mechanism during a selected period, wherein the factor of 2 is required only if a single force sensor is used.

9. The method as claimed in claim 8 further comprising:
   converting $F_{AVERAGE}$ to known units by multiplying a value of $F_{AVERAGE}$ by $M_{BINARY2NEWTONS}$, which is determined using:

$$M_{BINARY2NEWTONS} = (\text{Known\_Force}_{NEWTONS})/A\_TO\_D\_\text{Output}_{BINARY} \qquad \text{Eq. 10}$$

where: Known_Force$_{NEWTONS}$ is a predetermined force applied to the force sensor, and A_TO_D_Output$_{BINARY}$ is a binary output of the analog-to-digital converter when the predetermined force is applied.

10. The method as claimed in claim 9 further comprising:
    retrieving a length 'r' of the crank arm from memory and calculating $T_{AVERAGE}$ using:

$$T_{AVERAGE} = F_{AVERAGE} \cdot r \qquad \text{Eq. 8}$$

where: r=the length of the crank arm from crank arm shaft to pedal axis spindle; and
    converting cadence in RPM to cadence in RADs per second by multiplying cadence in revolutions per minute by $2\pi/360$.

11. The method as claimed in claim 10 further comprising:
    calculating $P_{AVERAGE}$ for each crank arm rotation using:

$$P_{AVERAGE} = T_{AVERAGE} \cdot \omega \qquad \text{Eq. 9.}$$

12. The method as claimed in claim 11 further comprising:
    using hysteresis to smooth data associated with the power applied to the pedal and crank arm based drive mechanism to decrease display jitter, and displaying the data for observation by the person.

* * * * *